(12) United States Patent
Griffin

(10) Patent No.: US 8,329,663 B2
(45) Date of Patent: Dec. 11, 2012

(54) COMPOSITIONS AND METHODS FOR THE TREATMENT OF CHRONIC INFECTIONS

(76) Inventor: Paul Griffin, Nashville, TN (US)

( * ) Notice: Subject to any disclaimer, the term of this patent is extended or adjusted under 35 U.S.C. 154(b) by 688 days.

(21) Appl. No.: 12/363,755

(22) Filed: Jan. 31, 2009

(65) Prior Publication Data

US 2009/0197822 A1 Aug. 6, 2009

Related U.S. Application Data

(60) Provisional application No. 61/024,905, filed on Jan. 31, 2008.

(51) Int. Cl.
*A61K 31/70* (2006.01)
*A61K 31/65* (2006.01)
(52) U.S. Cl. .......................... 514/29; 514/152
(58) Field of Classification Search .................. None
See application file for complete search history.

(56) References Cited

U.S. PATENT DOCUMENTS

| | | | |
|---|---|---|---|
| 4,740,372 A * | 4/1988 | Boncic ................. | 424/94.64 |
| 6,258,532 B1 | 7/2001 | Stratton et al. | |
| 6,340,463 B1 | 1/2002 | Mitchell et al. | |
| 6,562,582 B2 | 5/2003 | Mitchell et al. | |
| 6,579,854 B1 | 6/2003 | Mitchell et al. | |
| 6,664,239 B2 | 12/2003 | Mitchell et al. | |
| 6,710,033 B1 | 3/2004 | Stratton et al. | |
| 6,756,369 B2 | 6/2004 | Mitchell et al. | |
| 6,838,552 B1 | 1/2005 | Mitchell et al. | |
| 6,884,784 B1 | 4/2005 | Mitchell et al. | |
| 6,890,526 B2 | 5/2005 | Stratton et al. | |
| 6,927,227 B2 | 8/2005 | Robl et al. | |
| 2002/0016289 A1 | 2/2002 | Conneely et al. | |
| 2002/0049183 A1 | 4/2002 | Yedgar et al. | |
| 2004/0121979 A1 | 6/2004 | Susilo | |
| 2006/0003644 A1 | 1/2006 | Okabe | |
| 2007/0015718 A1 | 1/2007 | Mitchell et al. | |

* cited by examiner

*Primary Examiner* — Elli Peselev
(74) *Attorney, Agent, or Firm* — Luedeka Neely Group, P.C.

(57) ABSTRACT

The present disclosure provides compositions and methods for the treatment and elimination of chronic intracellular infections in cells or organisms. The compositions may include one or more acidic substances and one or more antimicrobial substances, administered in combination or separately. The methods may include administering an amount of one or more such compositions to an infected cell or organism for a period of time ranging from days to years, until the infection is substantially eliminated.

20 Claims, No Drawings

COMPOSITIONS AND METHODS FOR THE TREATMENT OF CHRONIC INFECTIONS

CROSS-REFERENCE TO RELATED APPLICATIONS

This application claims priority to U.S. Provisional Application No. 61/024,905, filed on Jan. 31, 2008.

TECHNICAL FIELD

The present disclosure relates to the treatment of chronic infectious pathogenic agents residing within cells of mammalian organisms, for example from within human or animal cells.

BACKGROUND

Some pathogens infect cells and populate the cells during one or more phases of their (i.e., the pathogen's) life cycle, which may include at lease one replicating phase. These pathogens, also called intracellular pathogens, may or may not be parasitic to the host cell. Sometimes a change in the intracellular environment of the host cell, for example host cell nutrient or energy depletion, may cause the pathogen or a portion of the population of the pathogen to undergo a morphological change from a replicating phase into a non-replicating, persistent phase, also known as the cryptic phase.

While the pathogen is in the persistent phase, the infected cell or organ may not exhibit any signs or symptoms of the infection. The pathogen may remain in the persistent phase for an indeterminate period of time, until the intracellular environment becomes favorable for pathogen replication again. At such time, the pathogen may revert to an antimicrobial-susceptible, replicating phase, and the organism may exhibit signs and symptoms of infection. The infection may also spread from one cell or organ to another cell or a cell of another organism.

Persistent phases of pathogens may generally be resistant to antimicrobial agents, while replication phases may generally be susceptible to antimicrobial agents. Thus, in order to effectively treat an infected cell or organism with an antimicrobial agent, it is necessary to cause the pathogen to transform from a persistent phase to a replicating phase.

One example of an infectious intracellular pathogen having a life cycle that includes both persistent and replicating phases is *Chlamydia pneumoniae* (hereafter "*C. pneumoniae*").

One known method for the detection and treatment of *C. pneumoniae* infections is described in U.S. Pat. No. 6,884,784 to Mitchell et al., filed Mar. 19, 2002, which is incorporated by reference herein. A disadvantage of the treatment disclosed therein is that it fails to adequately eliminate all of the cryptic phase of the infection in cells. Instead the method is focused on the administration of a combination of antimicrobial agents, over an extensive period of time, each directed toward a different phase of the *Chlamydia* life cycle.

The Chlamydiae family, of which *C. pneumoniae* are a member, are obligate intracellular prokaryotic microorganisms which parasitize eukaryotic cells and are ubiquitous throughout the animal kingdom. Members of the *Chlamydia* genus are considered bacteria with a unique multiphasic developmental cycle having distinct morphological and functional forms. This persistent developmental growth cycle alternates between 1) intracellular life forms, of which two are currently recognized, a metabolically-active, replicating organism known as the reticulate body ("RB") and a non-replicating organism known as the cryptic phase; and 2) an extracellular life form that is an infectious, metabolically-inactive form known as the elementary body ("EB"). Chlamydial EBs may be either intracellular or extracellular, while the replicating phase and cryptic phase are always intracellular.

EBs are small (300-400 nm) infectious, spore-like forms which are metabolically inactive, non-replicating, and found most often in the extracellular environment. EBs are resistant to a variety of physical insults such as enzyme degradation, sonication and osmotic pressure. This physical stability is believed to be a result of extensive disulfide cross-linking of the cysteine-rich major outer membrane protein ("MOMP").

When exposed to the oxidizing conditions in the extracellular environment of the host, the outer membrane of the EB is relatively impermeable, as well as resistant to inactivation. The EB is thus well suited to survive long enough outside of the host to be transmitted to a new host.

Infection by members of the genus *Chlamydia* may induce a significant inflammatory response at the cellular level. Despite this, clinically, the initial infection may vary frequently in the symptoms displayed, and may even be asymptomatic. Once fully established, *Chlamydia* species are difficult to eradicate, with frequent relapse following antibiotic therapy. Evidence also indicates that the *Chlamydia* may become dormant and may be shed in quantities too miniscule to reliably detect by culture.

*C. pneumoniae* is believed to cause, or contribute to, many chronic illnesses in mammals, and in particular humans. The current therapy for suspected/confirmed *C. pneumoniae* infection is with a short course (e.g., 2-3 weeks) of a single antibiotic. *C. pneumoniae* is susceptible in vitro to tetracycline, erythromycin, clarithromycin, and fluoroquinolones such as ofloxacin, levofloxacin, and sparfloxacin. Despite having this in vitro susceptibility, patients having *C. pneumoniae* infections may relapse following antibiotic therapy with these agents.

In vitro studies on the persistence of *Chlamydia* species, despite specific and appropriate antibiotic therapy, have suggested that the presence of antibiotics may promote the formation of a persistent intracellular, non-replicative state, typically referred to as the latent, persistent, or cryptic phase. This transformation can be thought of as a stringent response and may also be observed with nutrient starvation and exposure to γ-interferon. Thus, in this manner, the organism can escape antibiotic therapy as currently used in clinical practice.

In view of the chronic and persistent nature of *Chlamydia* infections, as well as the highly infective nature of *Chlamydia* EBs and their ability to reinfect cells, there is a need for antichlamydial therapy which totally or substantially eradicates the pathogen or population of pathogens from infected cells and/or organisms.

However, current medical practice does not provide any method suitable for the elimination of substantially all of a population of *Chlamydia* from an infected patient. Currently no method or composition is known that is able to eradicate the entire, or substantially entire, population of the pathogen in the cells. The failure of current treatments to accomplish such eradication is believed to be due to the resistance of the persistent phase to antimicrobial agents.

Accordingly, there is a need for more effective compositions and methods useful in the treatment of chronic intracellular infections, for example *C. pneumoniae* infections, which preferably do not cause undesirable side effects, yet are able to substantially eliminate the population of infectious agent from the organism.

SUMMARY

The present disclosure provides compositions and methods for treating and eliminating chronic infections in cells or organisms, and in particular, chronic intracellular infections where the infectious agent or pathogen may live within the cell in a persistent phase for an indeterminate period of time during the life cycle of the infectious agent.

In one embodiment of the present disclosure, a method for elimination of a persistent intracellular infection from within a cell may include a step of temporarily lowering the pH of a cell, the cell being infected by a pathogen in a persistent phase. This temporary pH depression is believed to induce the pathogen to undergo a morphological change from an antibiotic-resistant, persistent phase to an antibiotic-susceptible, replicating phase. The method also includes a subsequent step of providing one or more antimicrobial agents to the cell, thereby killing the pathogen. The steps may be repeated, in order, over a period of time, thereby totally or substantially eliminating the infection from the cell and/or organism.

In another embodiment of the present disclosure, a method for the elimination of a chronic *C. pneumoniae* infection from an organism may include the steps of temporarily lowering the pH of an infected host cell of an organism having at least one *C. pneumoniae* cell present in a persistent phase within the infected host cell. The pH depression may be accomplished by the administration of a composition as disclosed herein. Such temporary depression of the intracellular pH is believed to induce the *Chlamydia* to enter a replicating phase. The method further includes the subsequent step of contacting the *Chlamydia* with one or more antimicrobial agents. The steps may be repeated, in order, over a period of time, thereby eliminating the *Chlamydia* infection from the cells.

A further aspect of the present disclosure provides compositions for the elimination of chronic *C. pneumoniae* infections in infected host cells. In some embodiments the compositions may include one or more acidic substances and one or more antimicrobial agents.

Additional aspects and advantages of the disclosure will be set forth in part in the description which follows, and/or may be learned by practice of the disclosure. The aspects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

DETAILED DESCRIPTION

The present disclosure will now be described in the more limited aspects of preferred embodiments thereof, including various examples and illustrations of the formulation and use of the present disclosure. It will be understood that these embodiments are presented solely for the purpose of illustrating the invention and shall not be considered as a limitation upon the scope thereof.

The terms "susceptible" and "susceptibility" as used herein are intended to mean the physiological response of an organism to an environmental or chemical stimulus. The desired physiological response to stimuli is one which adversely affects the pathogen's viability to replicate or reside within the host cell and, ideally, would result in the reduction or complete elimination (i.e., death) of that pathogen.

In one embodiment of the present disclosure, a composition is disclosed for the elimination of a pathogen or a population of pathogens from an organism infected by the pathogen. The composition may completely or substantially eliminate the pathogenic infection.

The pathogen or one or more populations or subpopulations of the pathogen may reside intracellularly during at least a portion of the life cycle of the pathogen. For some pathogens, the pathogen or one or more populations or subpopulations of the pathogen may reside extracellularly during at least a portion of the life cycle of the pathogen. The pathogen may or may not be parasitic.

For example, the pathogen may be an obligate intracellular parasite having at least one persistent or cryptic phase, such as *C. pneumoniae*, which may also be referred to in the scientific literature as *Chlamydophila pneumoniae*. As mentioned above, the multiphasic developmental cycle of *C. pneumoniae* has distinct morphological and functional forms. The developmental growth cycle alternates between the intracellular phases (the RB and cryptic phases) and the extracellular, infectious EB phase. The cryptic phase is believed to be resistant to known antimicrobial agents.

Hence, in order to completely or substantially eliminate the infection, the cryptic phase as well as the EB and RB phases must be eliminated. Since the cryptic phase is believed to be resistant to known antimicrobial agents, it is desirable to induce the cryptic phase to undergo transformation into the reproductive, antibiotic susceptible RB phase.

It is believed that the *C. pneumoniae* in the cryptic phase may be "tricked" into sensing that the host cell may be dying, thus causing the pathogen to undergo transformation from the cryptic phase to the RB phase in an attempt to reproduce before the host cell dies. The death of the host cell would kill any obligate intracellular parasitic pathogen infecting the cell.

One indicator of impending cell death may be a sudden depression in the pH of the cytosol, which may be sensed by the pathogen and cause the pathogen to undergo a morphological change into a phase susceptible to one or more antimicrobial agents. Temporary pH depression of the cytosol may occur upon the uptake of acidic substances into the cell.

It is believed that even though the pH depression of the cytosol may induce the *Chlamydia* to transform from the cryptic phase into a susceptible phase, the buffering capabilities of the cell allow the pH to return to an acceptable level before significant damage to the cell may occur. It is believed that the *Chlamydia* undergo phase transformation more rapidly to the susceptible phase than back to the cryptic phase, and thus the antimicrobial agent is provided with a window of opportunity to attack the *Chlamydia*.

In one embodiment of the present disclosure, the composition may include at least one acidic substance and at least one antimicrobial agent.

A suitable acidic substance may have a pKa, as measured in water, of less than about 5.0. A partial list of some suitable acidic substances, and their pKa values, is provided in Table 1, below. Suitable acidic substances may include indole, caffeine, psilocybin, niacinamide and taurine. A particularly suitable acidic substance may be pyruvic acid, which may be in the form of calcium pyruvate or other pharmaceutically acceptable salt thereof. Some of the acidic substances may be polyprotic, as indicated by multiple pKa values listed for that substance. It is also desirable that the acidic substances be of low toxicity to the organisms or cells being treated.

TABLE 1

| Substance | pKa (in H$_2$O) |
|---|---|
| Indole | −3.6 |
| Psilocybin | 0.2 |
| Risedronic acid | 0.32, 5.09 |
| Tiludronic acid | 0.45 |
| Niacinamide | 0.5, 3.35 |
| Pyrazinamide | 0.5 |
| Hydralazine | 0.5 |
| Caffeine | 0.6, 14.0 |
| Sulfasalazine | 0.6 |
| Alatrofloxacin | 0.64, 8.12 |
| Bumetanide | 0.7 |
| Disulfiram | 0.86 |
| Cromolyn Sodium | 1.1 |
| Oxalic Acid | 1.27, 4.28 |
| Amifostine | 1.29, 10.16 |
| Dapsone | 1.3 |
| Taurine | 1.5 |
| Fluconazole | 1.5 (1.76) |
| Saccharin | 1.6 |
| Oxazepam | 1.7 |
| Flumazenil | 1.7 |
| Rifampin | 1.7, 7.9 |
| Colchicine | 1.7 |
| Amprenavir | 1.76, 11.54 |
| Hydroxyzine | 1.8 |
| Penicillamine | 1.8 |
| Isoniazid | 1.82 |
| Valacyclovir | 1.90, 7.47, 9.43 |
| Dimethyltryptamine | 2 |
| Cromoglycic acid | 2 |
| Vardenafil | 2.02, 6.13, 9.11 |
| Aminosalicylic acid | 2.05 |
| Phosphoric Acid | 2.12 |
| Cephapirin | 2.15, 5.44 |
| Dipicolinic Acid | 2.17, 4.97 |
| Cefoxitin | 2.2 |
| Ganciclovir | 2.2, 9.4 |
| Acyclovir | 2.27, 9.25 |
| Tinidazole | 2.34 |
| Pyruvate | 2.39 |
| Ranitidine | 2.4 |
| Methaqualone | 2.5 |
| Metronidazole | 2.5 |
| Cephradine | 2.6, 7.3 |
| Cobalamin | 2.7 |
| Clavulanic acid | 2.7 |
| Voriconazole | 2.72, 11.54 |
| 9-Hydroxy-risperidone | 2.77, 7.86 |
| Sodium | 2.8 |
| Sulphinpyrazone | 2.8 |
| Metformin | 2.8, 11.5 |
| Minocycline | 2.8, 5.0, 7.8 |
| Amoxicillin | 2.8, 7.2 |
| Pyrazinoic Acid | 2.9 |
| Ketoconazole | 2.9, 6.5 |
| Diflunisal | 2.94 |
| Ketoconazole | 2.94, 6.51 |
| Salicyclic Acid | 2.98 |
| Enalapril | 3.0, 5.4 |
| Diclofenac | 3 |
| Fumaric Acid | 3.02 |
| Ramipril | 3.1, 5.6 |
| Diazepam | 3.3, 4.69 |
| Tetracycline | 3.3, 7.68, 9.69 |
| Cefotaxime | 3.35 |
| Probenicid | 3.4 |
| Diazepam | 3.4 |
| Malic Acid | 3.4, 5.13 |
| Risperidone | 3.46, 7.89 |
| Acetylsalicylic acid | 3.49 |
| Ethacrynic Acid | 3.5 |
| Ketorolac | 3.5 |
| Doxycycline | 3.5, 7.7, 9.5 |
| Neurontin | 3.68, 10.70 |
| Itraconazole | 3.7 |
| Captopril | 3.7, 9.8 |
| Methyllactic Acid | 3.72 |
| Tiaprofenic acid | 3.8 |

TABLE 1-continued

| Substance | pKa (in H$_2$O) |
|---|---|
| L-carnitine | 3.8 |
| Methotrexate | 3.8, 4.8, 5.6 |
| Lactic Acid (Lactate) | 3.83 |
| Glycolic Acid | 3.83 |
| Timolol | 3.9 |
| Furosemide | 3.9, 9.9 |
| Flufenamic acid | 3.9 |
| Omeprazole | 4.0, 8.8 |
| Ascorbic Acid | 4.17, 11.6 |
| Succinic Acid | 4.19 |
| Naproxen | 4.2 |
| Mefenamic Acid | 4.2 |

Suitable antimicrobial agents for the practice of the present disclosure may include Rifamycins, such as rifampin, rifapentine, or rifabutin; Macrolides, such as chlarithromycin, azithromycin, or erythromycin; Quinolones, such as ofloxacin, levofloxacin, sparfloxacin, ciprofloxacin, lomefloxacin, moxifloxacin, or trovafloxacin; and Tetracyclines such as tetracycline, doxycycline, or minocycline. Other antimicrobial agents not listed here may also be suitable for the practice of the present disclosure, as long as the selected agent is effective against at least one phase in the life cycle of the pathogen desired to be eradicated.

One or more of the above acidic substances may be combined with one or more of the above antimicrobial substances to provide a unique pharmaceutical composition for treating chronic persistent infections, and in chronic particular *C. pneumoniae* infections. Alternatively, the two categories of substances may be administered as separate compositions, in which case they may or may not be administered simultaneously.

In addition to, or as part of, the present composition, other compounds may be co-administered to an individual undergoing antichlamydial therapy for the management of chronic/systemic infection.

For example, it may be desirable to include one or a combination of anti-inflammatory agents and/or immunosuppressive agents to ameliorate side-effects that may arise in response to a particular antimicrobial agent.

Suitable anti-inflammatory agents (steroidal and nonsteroidal agents) include, but are not limited to, prednisone, cortisone, hydrocortisone and naproxen. Preferably the anti-inflammatory agent is a steroidal agent, such as prednisone. The amount and frequency of administration of these adjunct compounds will depend upon patient health, age, clinical status and other factors readily apparent to the medical professional.

Pharmaceutical compositions for the treatment and elimination of infections as described herein may also contain inactive ingredients, such as excipients, binders, fillers, coatings, buffers, and the like. Such ingredients and their functions are well known to those of skill in the art and need not be discussed here.

A further aspect of the present disclosure provides a method for the treatment of chronic *C. pneumoniae* infections in organisms such as mammals, and in particular humans. The method may include the step of administering one or more compositions including at least one acidic agent and at least one antimicrobial agent, separately or in combination with one another, to an infected mammalian or human patient, over a period of time ranging from days to months, or from days to years. The method may eliminate substantially all of the *Chlamydia* from the infected patient.

The amount of acidic agent administered may range from about 1 mg to about 5 grams per day, and the amount of antimicrobial agent administered may range from about 1 mg to about 5 grams per day, depending on the particular agents used.

In some embodiments of the present disclosure, the method for treatment of chronic *C. pneumoniae* infections may include one or more treatment regimens, some examples of which are described below.

In one example, a patient infected with *C. pneumoniae*, was administered a treatment regimen that included about 500 mg per day of levofloxacin, about 100 mg per day of caffeine, and from about 5 mg to about 10 mg per day of prednisone. The treatment was administered from about 2 to about 3 years. Subsequent testing showed that substantially all of the *C. pneumoniae* were eliminated from the patient.

The following example treatment regimens were also tested and shown to reliably eradicate or substantially eliminate *C. pneumoniae* infections in human patients.

One suitable regimen may include about 150 mg rifabutin QD, or about 500 mg levofloxacin QD, or about 500 mg clarithromycin BD, or about 250 mg azithromycin 3 days per week; 100 mg caffeine QD increased by about 100 mg monthly (i.e. month 2, about 200 mg, month 3, about 300 mg, up to about 2 grams); and about 5-10 mg prednisone QD.

Another suitable regimen may include about 150 mg rifabutin QD, or about 500 mg levofloxacin QD, or about 500 mg clarithromycin BD, or about 250 mg azithromycin 3 days per week; about 81 mg acetylsalicylic acid titrated to about 2 grams (Month 1-about 81 mg, month 2-about 162 mg, etc.); and about 5-10 mg prednisone QD.

A further example treatment regime may include about 500 mg clarithromycin BD and about 20 mg omeprazole QD for about 3 months, and then increased to about 40 mg QD omeprazole.

Yet another example regime may include about 150 mg rifabutin QD, or about 500 mg levofloxacin QD, or about 500 mg clarithromycin BD, or about 250 mg azithromycin 3 days per week; about 20 mg furosemide QD titrated up to about 600 mg; and 5-10 mg prednisone QD.

The above described treatment regimens may be used over a period of 2-3 years. Typically a topical acidic agent could be used in conjunction with the antibiotic therapy. Topical creams, shampoos, and liquids have all been successfully tested. The best experience with these have been with a shampoo containing 3% salicylic acid and increased to 6% in month two and 9% in month three.

Furthermore, pyruvate has been used in conjunction with rifabutin, azithromycin, and levofloxacin in doses of about 1-5 grams daily. Calcium pyruvate is a suitable source of pyruvate.

Other embodiments of the present disclosure will be apparent to those skilled in the art from consideration of the specification and practice of the embodiments disclosed herein. As used throughout the specification and claims, "a" and/or "an" may refer to one or more than one. Unless otherwise indicated, all numbers expressing quantities of ingredients, properties such as molecular weight, percent, ratio, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. It is intended that the specification and examples be considered as exemplary only, with a true scope and spirit of the invention being indicated by the following claims.

The foregoing embodiments are susceptible to considerable variation in practice. Accordingly, the embodiments are not intended to be limited to the specific exemplifications set forth hereinabove. Rather, the foregoing embodiments are within the spirit and scope of the appended claims, including the equivalents thereof available as a matter of law.

The patentees do not intend to dedicate any disclosed embodiments to the public, and to the extent any disclosed modifications or alterations may not literally fall within the scope of the claims, they are considered to be part hereof under the doctrine of equivalents.

What is claimed is:

1. A method for the treatment of a population of a persistent intracellular *Chlamydia pneumonia* pathogen within a cell infected with the pathogen, wherein at least a portion of the population of the pathogen is in an persistent phase resistant to one or more antimicrobial agents, said method comprising the steps of:

temporarily lowering the pH of a cell infected with *Chlamydia pneumonia* existing in an intracellular persistent cryptic phase using at least one acidic agent, wherein the intracellular pathogen is transformed from the persistent phase into an replicating phase susceptible to one or more antimicrobial agents; and providing at least one antimicrobial agent to the infected cell, wherein the agent kills the pathogen but not the infected cell, transforming the infected cell into a non-infected cell.

2. The method of claim 1, wherein the acidic agent comprises at least one substance selected from the group consisting of caffeine, taurine, pyruvic acid, calcium pyruvate, indole, salicylic acid, and psilocybin.

3. The method of claim 1, wherein the antimicrobial agent comprises at least one substance selected from the group consisting of rifabutin, tetracycline, erythromycin, clarithromycin, ofloxacin, levofloxacin, and sparfloxacin.

4. The method of claim 1, further comprising a step of providing at least one anti-inflammatory agent to the infected cell.

5. The method of claim 4, wherein the anti-inflammatory agent comprises at least one agent selected from the group consisting of prednisone, cortisone, hydrocortisone and naproxen.

6. A method for the treatment of a persistent intracellular *Chlamydia pneumonia* infection of at least a portion of a population of a pathogen in an organism, wherein the method comprises the steps of:

administering to the organism at least one acidic composition in an amount sufficient to temporarily depress the intracellular pH of a cell of the organism infected with *Chlamydia pneumonia* existing in an intracellular persistent cryptic phase, and induce the intracellular pathogen into an antimicrobial-susceptible replicating phase; and administering to the organism at least one antimicrobial composition while the intracellular pH is depressed, in an amount sufficient to kill the pathogen but not the cell of the organism, thereby eliminating the pathogen from the organism.

7. The method of claim 6, wherein the acidic agent comprises at least one substance selected from the group consisting of caffeine, taurine, pyruvic acid, calcium pyruvate, indole, salicylic acid, and psilocybin.

8. The method of claim 6, wherein the antimicrobial agent comprises at least one substance selected from the group consisting of rifabutin, tetracycline, erythromycin, clarithromycin, ofloxacin, levofloxacin, and sparfloxacin.

9. The method of claim 6, further comprising a step of providing at least one anti-inflammatory agent to the infected cell.

10. The method of claim 6, wherein the anti-inflammatory agent comprises at least one agent selected from the group consisting of prednisone, cortisone, hydrocortisone and naproxen.

11. A method for the treatment of a persistent intracellular infection *Chlamydia pneumonia* of at least a portion of a population a pathogen in an organism, wherein the method comprises the steps of:
   a. administering to the organism at least one acidic composition in an amount sufficient to make the intracellular pathogen antimicrobial-susceptible, wherein the intracellular pathogen consists essentially of *Chlamydia pneumonia*; and
   b. administering to the organism at least one antimicrobial composition while the pathogen is antimicrobial-susceptible, in an amount sufficient to kill the pathogen but not the cell of the organism, thereby eliminating the pathogen from the organism.

12. The method of claim 11 wherein the acidic composition has a pKa of less than about 5.0 in water and is repetitively administered to the organism with the dosage increasing over time and wherein the antimicrobial composition is repeatedly administered at about the same time as the repetitive doses of the acidic composition.

13. The method of claim 11 wherein the acidic composition is caffeine administered each day with the dosage per day beginning at a tolerated amount and increasing about 100 mg each month until the dosage reaches about 2 grams per day.

14. The method of claim 11 comprising a treatment regimen of about 500 mg per day of levofloxacin, about 100 mg per day of caffeine, and from about 5 mg to about 10 mg per day of prednisone administered until testing shows that substantially all of the pathogen are eliminated from the organism.

15. The method of claim 11 comprising a treatment regimen of:
   a. about 150 mg rifabutin QD, or about 500 mg levofloxacin QD, or about 500 mg clarithromycin BD, or about 250 mg azithromycin 3 days per week;
   b. about 100 mg caffeine QD increased by about 100 mg monthly (i.e. month 2, about 200 mg, month 3, about 300 mg, up to about 2 grams); and
   c. about 5-10 mg prednisone QD.

16. The method of claim 11 comprising a treatment regimen of:
   a. about 150 mg rifabutin QD, or about 500 mg levofloxacin QD, or about 500 mg clarithromycin BD, or about 250 mg azithromycin 3 days per week;
   b. about 81 mg acetylsalicylic acid titrated to about 2 grams (Month 1—about 81 mg, month 2—about 162 mg, etc.); and
   c. about 5-10 mg prednisone QD.

17. The method of claim 11 comprising a treatment regimen of:
   a. about 500 mg clarithromycin BD;
   b. about 20 mg omeprazole QD for about 3 months, and
   c. then increased to about 40 mg QD omeprazole.

18. The method of claim 11 comprising a treatment regimen of:
   a. about 150 mg rifabutin QD, or about 500 mg levofloxacin QD, or about 500 mg clarithromycin BD, or about 250 mg azithromycin 3 days per week;
   b. about 20 mg furosemide QD titrated up to about 600 mg; and
   c. about 5-10 mg prednisone QD.

19. The method of claim 11 comprising a treatment regimen of a topical acidic agent used in conjunction with the antimicrobial composition.

20. The method of claim 11 comprising a treatment regimen including pyruvate in doses of about 1-5 grams daily combined with administering rifabutin, azithromycin, or levofloxacin.

* * * * *